(12) United States Patent
McGee et al.

(10) Patent No.: US 9,750,426 B2
(45) Date of Patent: Sep. 5, 2017

(54) SYSTEM AND METHOD FOR ASSESSING RESPONSE TO CHEMOTHERAPY USING MAGNETIC RESONANCE ELASTOGRAPHY

(75) Inventors: Kiaran P McGee, Rochester, MN (US); Richard L Ehman, Rochester, MN (US); Stephen M Ansell, Rochester, MN (US); Yogesh K Mariappan, Rochester, MN (US); Jun Chen, Rochester, MN (US)

(73) Assignee: MAYO FOUNDATION FOR MEDICAL EDUCATION AND RESEARCH, Rochester, MN (US)

( * ) Notice: Subject to any disclaimer, the term of this patent is extended or adjusted under 35 U.S.C. 154(b) by 687 days.

(21) Appl. No.: 13/301,300

(22) Filed: Nov. 21, 2011

(65) Prior Publication Data
US 2012/0130227 A1    May 24, 2012

Related U.S. Application Data

(60) Provisional application No. 61/415,658, filed on Nov. 19, 2010.

(51) Int. Cl.
*A61B 5/055* (2006.01)
*A61B 5/00* (2006.01)

(52) U.S. Cl.
CPC ............ *A61B 5/055* (2013.01); *A61B 5/0051* (2013.01)

(58) Field of Classification Search
CPC .... G01R 33/56358; A61B 5/055; A61B 8/485
USPC .......................................... 600/407, 410–423
See application file for complete search history.

(56) References Cited

U.S. PATENT DOCUMENTS 5,592,085 A    1/1997 Ehman
7,166,075 B2 *  1/2007 Varghese et al. ............. 600/439

OTHER PUBLICATIONS

"Magnetic resonance elastography: Non-invasive mapping o tissue elasticity" by A. Manduca et al. Medical Image Analysis. 5:237-254. 2001.*

(Continued)

*Primary Examiner* — Tse Chen
*Assistant Examiner* — Jason Ip
(74) *Attorney, Agent, or Firm* — Quarles & Brady LLP (57) ABSTRACT

A system and method for determining a response of a tumor following a chemotherapy process includes the use of a magnetic resonance elastography (MRE) driver and a magnetic resonance imaging (MRI) system. The method includes controlling the MRE driver and the MRI system to acquire raw MRE data from the tumor, inverting the raw MRE data to produce an elastogram of the tumor, and determining a response of the tumor to the chemotherapy process from the elastogram.

9 Claims, 6 Drawing Sheets (56) References Cited

OTHER PUBLICATIONS

"MRI Measurements of Breast Tumor Volume Predict Reponse to Neoadjuvant Chemotherapy and Recurrence-Free Survival" by S.C. Partridge et al. American J Roentgenology. 184:6. pp. 1774-1781. 2005.*

Chaosuwannakit, et al., Aortic Stiffness Increases Upon Receipt of Anthracycline Chemotherapy, Journal of Clinical Oncology, 2010, 28(1):166-172.

Lam, et al., Chemotherapy Exposure Increases Leukemia Cell Stiffness, Blood, 2007, 109(8):3505-3508.

Manduca, et al., Magnetic Resonance Elastography: Non-invasive Mapping of Tissue Elasticity, Medical Image Analysis, 2001, 5:237-254.

Murayama, et al., Development of a New Instrument for Examination of Stiffness in the Breast Using Haptic Sensor Technology, Sensors and Actuators A, 2008, 143:430-438.

* cited by examiner

SYSTEM AND METHOD FOR ASSESSING RESPONSE TO CHEMOTHERAPY USING MAGNETIC RESONANCE ELASTOGRAPHY

CROSS-REFERENCE TO RELATED APPLICATIONS

This application is based on, claims priority to, and incorporates herein by reference U.S. Provisional Patent Application Ser. No. 61/415,658 filed on Nov. 19, 2011, and entitled "SYSTEM AND METHOD FOR ASSESSING TUMOR RESPONSE TO CHEMOTHERAPY USING MAGNETIC RESONANCE ELASTOGRAPHY."

STATEMENT REGARDING FEDERALLY SPONSORED RESEARCH

This invention was made with government support under grant number NIH EB001981, awarded by the National Institutes of Health. The government has certain rights in the invention.

BACKGROUND OF THE INVENTION

In the treatment of various cancers, chemotherapy is considered to be an effective therapeutic option. However, chemotherapeutic agents generally lack targeting specificity due to their inability to differentiate between normal or benign and malignant neoplasms undergoing rapid cellular division. As a consequence, these agents have significant normal tissue toxicity that include, but are not limited to, decreased erythrocyte, leukocyte, and platelet counts, nausea, vomiting, hair loss, and fatigue.

To maximize the prognostic outcomes in cancer patients, an optimal chemotherapeutic agent, in which the therapeutic ratio (tumor cell kill/normal tissue sparing) is very high, needs to be used. As known in the art, the selection of an optimal agent is based on a search to balance a marked growth-inhibitory or controlling effect on the cancer cell with the toxic effect on the host. While agent optimization is a complex process of basic science, research, and discovery involving cell biologists, chemists, pharmacologists, and physicians, a practical clinical approach is to develop methods that can more rapidly evaluate treatment efficacy following chemotherapy administration. Early identification of a poor responder allows the treatment to be modified, which can increase the potential for improved outcomes in these patients.

Thus, it is very important to monitor tumor response early in a chemotherapy process to identify and optimize the use of the chemotherapeutic agent for individual patients. Traditionally, monitoring has involved analysis of response by volumetric assessment, which is performed by evaluating changes in the tumor volume by direct physical or imaging-based measurement. Unfortunately, this process has an inherent latency due to the delay between chemotherapy administration and detection of gross tumor change during which time the therapeutic ratio might be reduced by non-specific targeting of the chemotherapy to rapidly dividing normal tissues, such as those within the oral cavities and hair.

As a specific example, there is evidence within patients with lymphoma to indicate that early response to chemotherapy, as measured by positron emission tomography (PET), using F-18 Fluorodeoxygluocose, is strongly correlated with improved treatment outcome. PET imaging is typically performed before initiation of chemotherapy to establish a metabolic baseline for the tumor and to provide a measure of overall size (i.e. volume). A second scan is performed after the administration of chemotherapy to assess treatment efficacy. However, this "early" assessment of treatment response is typically performed after two cycles of chemotherapy, typically six weeks following initiation of treatment. Unfortunately, the four to six week interval that normally applies for FDG-PET monitoring of tumor response presents a substantial impediment to effectively identifying non responders. Thus, the standard method of assessing response to chemotherapy is through the use of PET; however, this method is typically performed after two cycles of chemotherapy, during which time significant normal tissue toxicity is commonly observed.

Therefore, it would be desirable to have a system and method to test the effectiveness of chemotherapy administered to a patient as early as possible, while still differentiating between responders and non-responders. Such systems and methods enabling the early identification of poor responders allows for earlier treatment modification, thereby increasing the potential for improved outcomes in these patients.

SUMMARY OF THE INVENTION

The present invention overcomes the aforementioned drawbacks by providing a system and method for performing early monitoring of chemotherapy response using magnetic resonance elastography (MRE)-based estimates of shear modulus. Specifically, the present invention employs MRE to monitor for changes in the mechanical properties of tumors within a time interval ranging from several hours to days following chemotherapy to determine a relative effectiveness of the chemotherapy. The ability to identify both responders and non-responders to chemotherapy substantially immediately following treatment allows clinicians to tailor therapies on a patient-by-patient basis in addition to reducing the many normal tissue toxicities encountered over a typical four-to-six week interval.

In accordance with one aspect of the present invention, a method is disclosed for assessing an effectiveness of chemotherapy on a tumor within a subject following the administration of the chemotherapy to the subject. The method includes arranging the subject within a magnetic resonance imaging (MRI) system, coupling to the subject a magnetic resonance elastography (MRE) driver and controlling the MRE driver and the MRI system using a pulse sequence to acquire raw MRE data from the tumor. The method also includes inverting the raw MRE data to produce an elastogram of the tumor, selecting a region of interest in the elastogram, determining a stiffness within at least a portion of the region of interest, and indicating a response of the tumor to the chemotherapy.

In accordance with another aspect of the present invention, a magnetic resonance imaging (MRI) system is disclosed that includes a magnet system configured to generate a polarizing magnetic field about at least a portion of a subject having a tumor had having received a dose of chemotherapy, the subject and tumor arranged in the MRI system and a plurality of gradient coils configured to apply a gradient field to the polarizing magnetic field. The MRI system also include a radio frequency (RF) system configured to apply an excitation field to the subject and acquire MR image data therefrom and a driver system configured to deliver an oscillatory stress to the subject to, thereby, direct a shear wave toward the tumor. The MRI system further includes a computer system programmed to control operation of the plurality of gradient coils, RF system, and driver system to acquire medical imaging data, invert the medical imaging data to produce an elastogram of the subject illustrating the tumor, and indicate an effectiveness of the chemotherapy on the tumor.

In accordance with still another aspect of the present invention, a method for determining a response of a tumor following a chemotherapy process includes arranging the tumor proximate to a magnetic resonance elastography (MRE) driver and within a magnetic resonance imaging (MRI) system. The method also includes controlling the MRE driver and the MRI system using a pulse sequence to acquire raw MRE data from the tumor, inverting the raw MRE data to produce an elastogram of the tumor, and determining a response of the tumor to the chemotherapy process from the elastogram.

The foregoing and other aspects of the invention will be made apparent from the following description. In the description, reference is made to the accompanying drawings that form a part hereof, and in which there is shown by way of illustration a preferred embodiment of the invention. Such embodiment does not necessarily represent the full scope of the invention, however, and reference is made therefore to the claims and specification as a whole for interpreting the scope of the invention.

BRIEF DESCRIPTION OF THE DRAWINGS

FIG. 5a is $T_1$ weighted image of a tumor after chemotherapy, FIG. 5b is a shear wave image of the tumor of FIG. 5a acquired using a frequency of 1 kHz. FIG. 5c is an elastogram of the tumor of FIGS. 5a and 5b, FIG. 5d is a $T_1$ weighted image of a tumor after receiving a does of saline, FIG. 5e is a shear wave image of the tumor of FIG. 5d acquired using a frequency of 1 kHz, and FIG. 5f is an elastogram of the tumor of FIGS. 5d and 5e.

DETAILED DESCRIPTION OF THE INVENTION

When a substance such as human tissue is subjected to a uniform magnetic field (polarizing field $B_0$), the individual magnetic moments of the excited nuclei in the tissue attempt to align with this polarizing field, but precess about it in random order at their characteristic Larmor frequency. If the substance, or tissue, is subjected to a magnetic field (excitation field $B_1$) that is in the x-y plane and that is near the Larmor frequency, the net aligned moment, $M_z$, may be rotated, or "tipped", into the x-y plane to produce a net transverse magnetic moment $M_t$. A signal is emitted by the excited nuclei or "spins", after the excitation signal $B_1$ is terminated, and this signal may be received and processed to form an image.

When utilizing these "MR" signals to produce images, magnetic field gradients ($G_x$, $G_y$, and $G_z$) are employed. Typically, the region to be imaged is scanned by a sequence of measurement cycles in which these gradients vary according to the particular localization method being used. The resulting set of received MR signals are digitized and processed to reconstruct the image using one of many well known reconstruction techniques.

Figure 1:
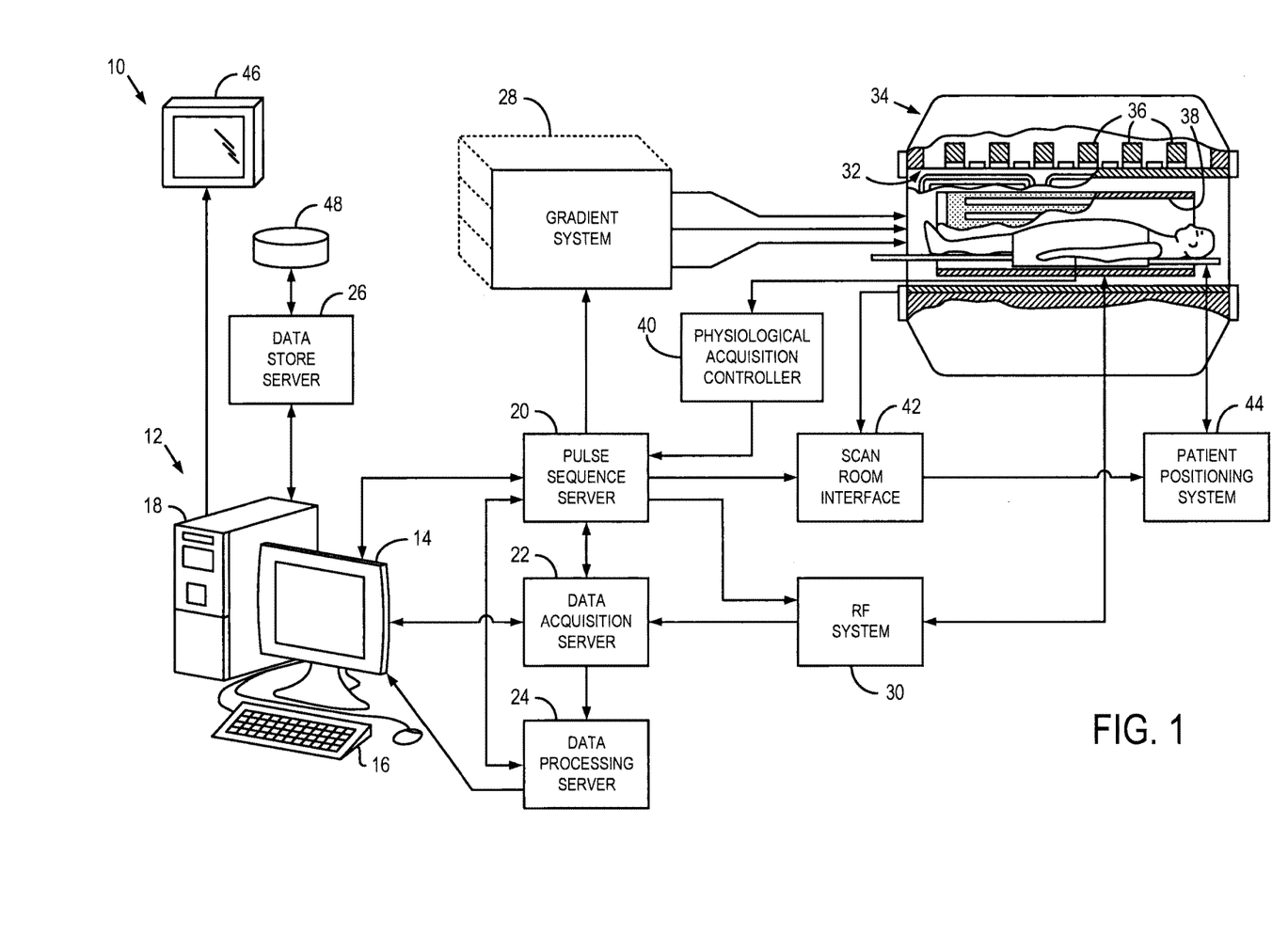
FIG. 1 is a schematic diagram of a magnetic resonance imaging (MRI) system for use with the present invention.

Specifically, referring to FIG. 1, the present invention may be employed using an MRI system 10. The MRI system 10 includes a workstation 12 having a display 14 and a keyboard 16. The workstation 12 includes a processor 18 that is a commercially available programmable machine running a commercially available operating system. The workstation 12 provides the operator interface that enables scan prescriptions to be entered into the MRI system 10. The workstation 12 is coupled to, for example, four servers including a pulse sequence server 20, a data acquisition server 22, a data processing server 24, and a data storage server 26. The workstation 12 and each server 20, 22, 24, and 26 are connected to communicate with each other.

The pulse sequence server 20 functions in response to instructions downloaded from the workstation 12 to operate a gradient system 28 and an RF system 30. Gradient waveforms necessary to perform the prescribed scan are produced and applied to the gradient system 28 that excites gradient coils in an assembly 32 to produce the magnetic field gradients $G_x$, $G_y$, and $G_z$ used for position encoding MR signals. The gradient coil assembly 32 forms part of a magnet assembly 34 that includes a polarizing magnet 36 and a whole-body RF coil 38.

RF excitation waveforms are applied to the RF coil 38 by the RF system 30 to perform the prescribed magnetic resonance pulse sequence. Responsive MR signals detected by the RF coil 38 or a separate local coil (not shown in FIG. 1) are received by the RF system 30, amplified, demodulated, filtered, and digitized under direction of commands produced by the pulse sequence server 20. As will be described in detail with respect to FIG. 2, the RF system 30 includes an RF transmitter for producing a wide variety of RF pulses used in MR pulse sequences, which is responsive to the scan prescription and direction from the pulse sequence server 20 to produce RF pulses of the desired frequency, phase, and pulse amplitude waveform. The generated RF pulses may be applied to the whole body RF coil 38 or to one or more local coils or coil arrays (not shown in FIG. 1).

The RF system 30 also includes one or more RF receiver channels. Each RF receiver channel includes an RF amplifier that amplifies the MR signal received by the coil to which it is connected and a detector that detects and digitizes the I and Q quadrature components of the received MR signal. The magnitude of the received MR signal may thus be determined at any sampled point by the square root of the sum of the squares of the I and Q components:

$$M=\sqrt{I^2+Q^2},$$

and the phase of the received MR signal may also be determined:

$$\phi=\tan^{-1}Q/I.$$

The pulse sequence server 20 also optionally receives patient data from a physiological acquisition controller 40. The physiological acquisition controller 40 receives signals from a number of different sensors connected to the patient, such as ECG signals from electrodes or respiratory signals from a bellows. Such signals are typically used by the pulse sequence server 20 to synchronize, or "gate", the performance of the scan with the subject's respiration, heart beat, or the like.

The pulse sequence server 20 also connects to a scan room interface circuit 42 that receives signals from various sensors associated with the condition of the patient and the magnet system. It is also through the scan room interface circuit 42 that a patient positioning system 44 receives commands to move the patient to desired positions during the scan.

The digitized MR signal samples produced by the RF system 30 are received by the data acquisition server 22. The data acquisition server 22 operates in response to instructions downloaded from the workstation 12 to receive the real-time MR data and provide buffer storage such that no data is lost by data overrun. In some scans, the data acquisition server 22 does little more than pass the acquired MR data to the data processor server 24. However, in scans that require information derived from acquired MR data to control the further performance of the scan, the data acquisition server 22 is programmed to produce such information and convey it to the pulse sequence server 20. For example, during prescans, MR data is acquired and used to calibrate the pulse sequence performed by the pulse sequence server 20. Also, navigator signals may be acquired during a scan and used to adjust RF or gradient system operating parameters or to control the view order in which k-space is sampled. And, the data acquisition server 22 may be employed to process MR signals used to detect the arrival of contrast agent in an MRA scan. In all these examples, the data acquisition server 22 acquires MR data and processes it in real-time to produce information that is used to control the scan.

The data processing server 24 receives MR data from the data acquisition server 22 and processes it in accordance with instructions downloaded from the workstation 12. Such processing may include, for example, Fourier transformation of raw k-space MR data to produce two or three-dimensional images, the application of filters to a reconstructed image, the performance of a backprojection image reconstruction of acquired MR data, the calculation of functional MR images, the calculation of motion or flow images, and the like.

Images reconstructed by the data processing server 24 are conveyed back to the workstation 12 where they are stored. Real-time images are stored in a database memory cache (not shown) from which they may be output to the display 14 or a display 46 that is located near the magnet assembly 34 for use by attending physicians. Batch mode images or selected real time images are stored in a host database on disc storage 48. When such images have been reconstructed and transferred to storage, the data processing server 24 notifies the data store server 26 on the workstation 12. The workstation 12 may be used by an operator to archive the images, produce films, or send the images via a network to other facilities.

It has been found that MR imaging can be enhanced when an oscillating stress is applied to the object being imaged in a method called MR elastography (MRE). The method uses an oscillating stress to produce shear waves that propagate through the organ, or tissues to be imaged. These shear waves alter the phase of the MR signals, and from this the mechanical properties of the subject can be determined. In many applications, the production of shear waves in the tissues is merely a matter of physically vibrating the surface of the subject with an electromechanical device such as that disclosed in U.S. Pat. No. 5,592,085, which is incorporated herein by reference. Shear waves may also be produced in the breast and prostate by direct contact with the oscillatory device. Also, with organs like the liver, the oscillatory force can be directly applied by means of an applicator that is inserted into the organ.

Figure 2:
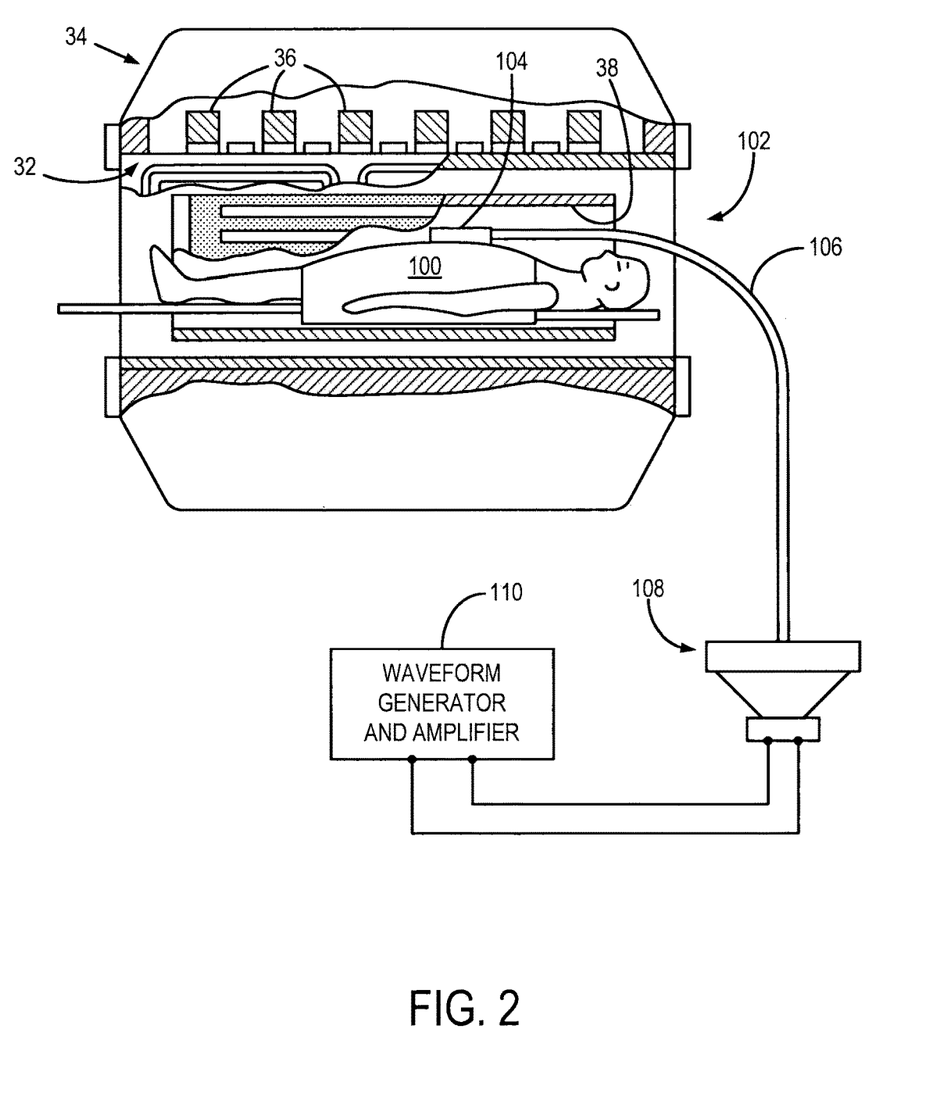
FIG. 2 is a schematic diagram of a sub-system of the MRI system of FIG. 1 including an MRI bore and magnetic resonance elastography (MRE) driver system.

Referring particularly to FIG. 2, a subject to be examined 100 is placed in the bore of the MRI system magnet 34 and is subjected to magnetic fields produced under the direction of a selected pulse sequence. An MRE driver system 102 is used to impart vibrational energy. As will be described, the MRE driver system 102 is a powerful, high-frequency driver system configured to deliver high-frequency shear waves to a small tumor within the subject 100.

The MRE driver system may include an active driver, such as will be described with respect to FIGS. 3a and 3b, or as illustrated in FIG. 2, a passive actuator 104 that is positioned over the region of interest in the subject 100 and is connected by way of a tube 106 to a remotely-located driver assembly 108. The passive driver 104 has a membrane that is vibrated by this acoustic wave to stress tissues against which it bears. The driver assembly 108 is remote from the magnet 34 in the sense that it is away from the strong magnetic fields produced by the magnet 36 where its operation is not impeded by those fields, and where its operation will not perturb the MRI system magnetic fields. The driver assembly 102 is electrically driven by a waveform generator and amplifier 110, which in turn is controlled by the pulse sequence server 20 of FIG. 1.

The pulse sequence server 20 of FIG. 1 directs the MRI system to perform an MRE pulse sequence, and in doing so it outputs synchronizing pulses to the waveform generator and amplifier 110. As will be described, the sync pulses are used to enable the waveform generator 110 to produce an oscillatory signal at the proper moment during each MRE pulse sequence. This signal energizes a loudspeaker in the driver assembly 108 to produce acoustic waves that are coupled to the passive driver 104 through the tube 106.

Figure 3:
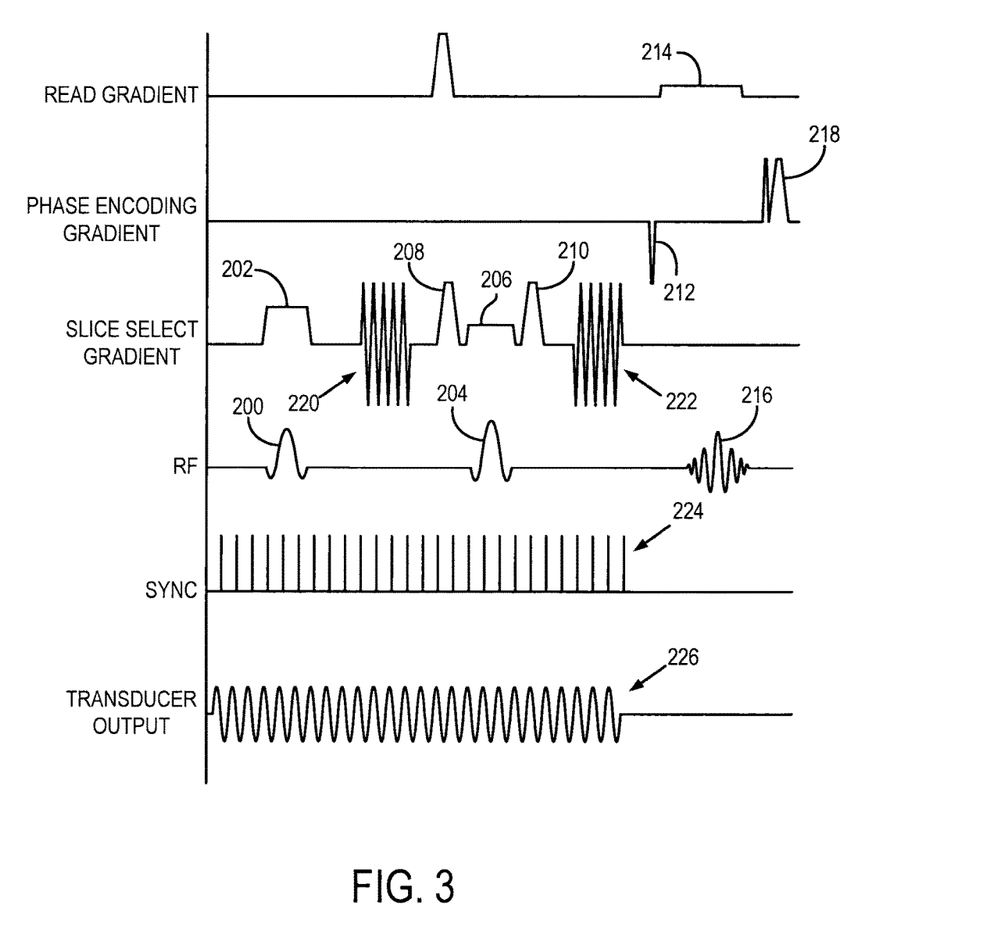
FIG. 3 is a pulse sequence diagram illustrating an MRE pulse for use with the present invention.

Referring to FIG. 3, in accordance with the present invention, a high-frequency MRE, spin echo (SE) pulse sequence may be utilized so as to provide sufficient phase-signal-to-noise ratio to image high frequency shear waves in the tumor within the subject 100 of FIG. 2. It should be noted that a SE pulse sequence is provided for exemplary purposes and the present invention may utilize other pulse sequences, such as gradient echo pulse sequences. Continuing with respect to FIG. 3, the pulse sequence is fundamentally a 2DFT pulse sequence using a spin-echo. Transverse excitation is produced by a 90 degree RF excitation pulse 200 in the presence of a slice-select gradient ($G_z$) pulse 202. A 180 degree RF refocusing pulse 204 is then applied in the presence of slice-selection gradient 206. To substantially reduce unwanted phase dispersions, a first crusher gradient 208 bridges the slice-selective gradient 206 with a second crusher gradient 210. A phase encoding gradient ($G_y$) pulse 212 is applied at an amplitude and polarity determined by the view number of the acquisition. A positive readout gradient pulse 214 is applied and an NMR signal 216 is acquired to frequency encode digitized samples. The pulse sequence concludes with a rephasing pulse 218 along the phase encoding axis.

To practice the present invention, an alternating magnetic field gradient is applied after the transverse magnetization is produced and before the NMR signal is acquired. The slice-select gradient ($G_z$) is used for this function and is alternated in polarity to produce a first set of bipolar gradient waveforms 220 before the application of the 180 degree refocusing pulse 204, and a second set of bipolar gradient waveforms 222 after the application of the 180 degree refocusing pulse 204. These gradient waveforms are referred to as motion-encoding gradient (MEG) waveforms. The second set of MEG waveforms 220 are played out 180 degrees out of phase with the first set of bipolar gradient waveforms 222 so that phase is properly accumulated. Typically, 1-10 cycles of these MEG waveforms with frequencies ranging from 50 to 200 Hz are included in the pulse sequence, depending upon the clinical application. However, it is contemplated that the present invention may advantageously utilize a high-frequency pulse sequence and, thus, a substantially higher frequency MEG waveform may be used. For example, the MEG waveforms may have a frequency on the order of, for example, 800 Hz to a kilohertz, and even higher. Regardless of the specific frequency selected, the pulse sequence server 20 of FIG. 1 produces sync pulses 224 that are at the same selected frequency and have a specific phase relationship with the alternating gradient pulses 220 and 222. As will be explained below, these sync pulses 224 activate a transducer to apply an oscillating stress 226 to the patient, which generally has the same frequency and phase relationship as the MEG waveforms. To ensure that the resulting waves have time to propagate throughout the field of view, the sync pulses 224 may be turned on well before the pulse sequence begins, as is shown in FIG. 3.

The phase of the NMR signal 216 is indicative of the movement of the spins. If the spins are stationary, the phase of the NMR signal 216 is not altered by the MEG pulses 220 and 222, whereas spins moving along the direction of the motion encoding gradient will accumulate a phase proportional to their displacement. Spins that move in synchronism and in phase with the alternating magnetic field gradients 220 and 222 will accumulate maximum phase of one polarity, and those that move in synchronism, but 180 degrees out of phase with the alternating magnetic field gradients 220 and 222 will accumulate maximum phase of the opposite polarity. The phase of the acquired NMR signal 216 is thus affected by the "synchronous" movement of spins along the motion encoded direction.

It is noted that the pulse sequence in FIG. 3 can be modified to measure synchronous spin movement along the other gradient axes. For example, the MEG waveforms 220, 222 may be applied along the phase encoding axis or they may be applied along the slice select axis. Indeed, they may be applied simultaneously to two or three of the gradient field directions to "read" synchronous spin movements along any desired direction. In addition, a $T_1$-weighted spin echo based sequence may be used to acquire high-resolution anatomic images of the tumor. As noted above, this is provided for exemplary purposes and the present invention may utilize other pulse sequences Referring now to FIG. 4, the aforementioned systems and control method may be used to perform a process for monitoring the response of a subject to chemotherapy using magnetic resonance elastography (MRE)-based estimates of shear modulus. The process 230 starts at process block 232 with either the positioning of the subject in the bore of an MRI system and the coupling of an MRE drive or the positioning of an ex viva sample within an MRE system. As described, the present invention, is capable of assessing the response of a tumor to chemotherapy, comparatively, immediately following thereafter. Thus, the step of positioning the subject for imaging at process block 232 may be initiated within hours to days after the completion of chemotherapy, instead of weeks later, as required in traditional assessment techniques. Once the subject is positioned for MRE imaging, using a high-frequency pulse sequence, such as the example sequence described with respect to FIG. 3, raw MRE data is collected from the subject or sample at process block 234.

Figure 4:
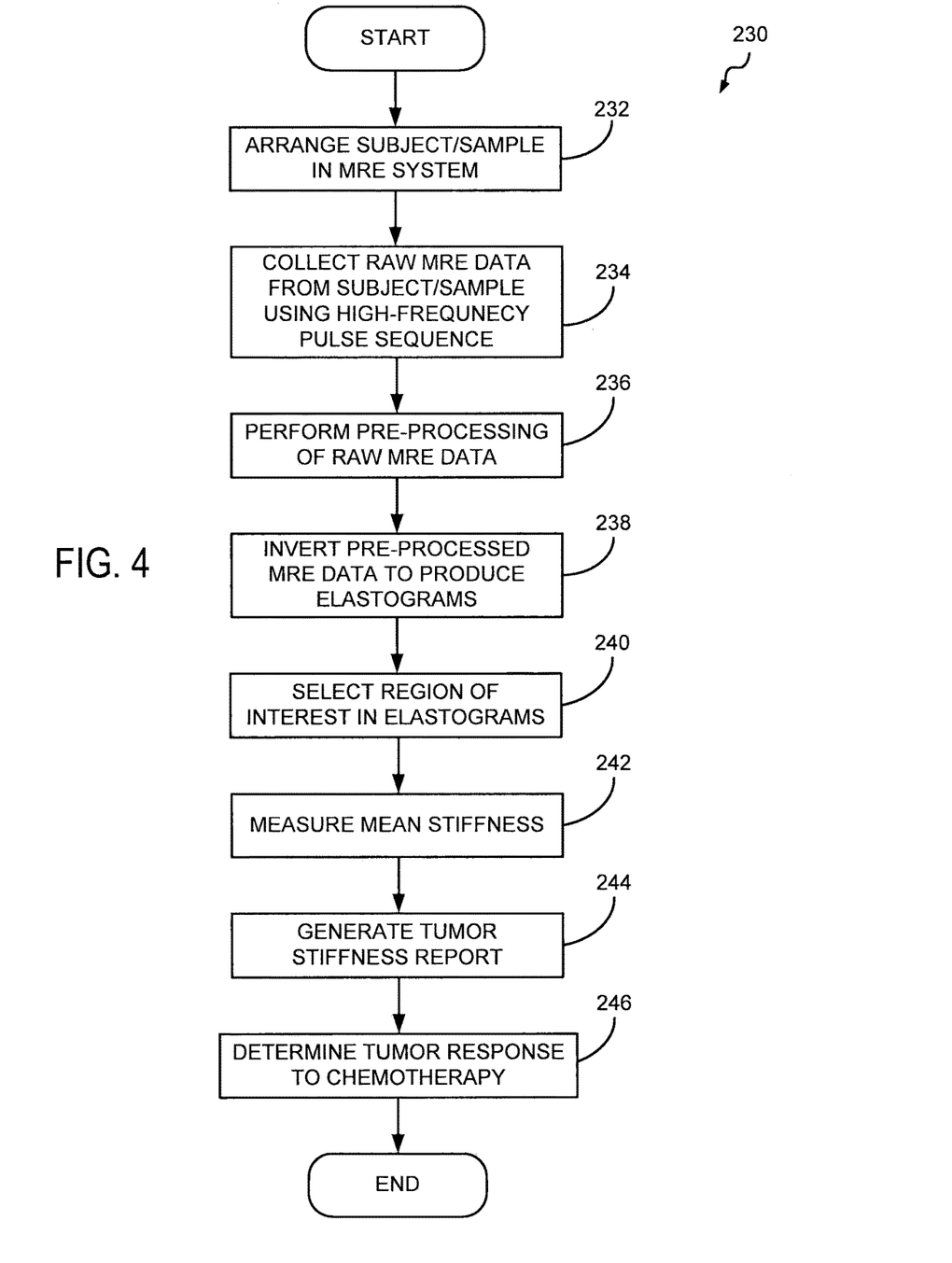
FIG. 4 is a flow chart setting forth the steps of a process for analyzing the effectiveness of chemotherapy in accordance with the present invention.

After the raw MRE data is collected at process block 234, the data is pre-processed at process block 236. Pre-processing may include minimum discontinuity phase unwrapping, 2-dimensional filtering along, for example, eight evenly spaced directions in the imaging plane and 2-dimensional order-4 Butterworth bandpass filtering with cutoff wave numbers of 1 and 80 waves/FOV. Then, at process block 238, a 2-D phase gradient inversion is used to process the preprocessed data and produce elastograms. The phase gradient inversion may be done, for example, with a 5×5 window. Using the elastograms, at process block 240, regions of interest (ROIs) can be drawn on the tumor where wave penetration and phase signal to noise ratio were visually acceptable. Using the selected ROIs, the mean stiffness values in these regions of interest can then be measured for each slice, at process block 242, and the average of these values can then be reported as a stiffness value of tumors, at process block 244. Using this information, a determination of the response of the tumor to the chemotherapy can be determined.

For example, following chemotherapy, the tumor will generally increase in stiffness. However, it is noted that the change parameters will vary as a function of delay from the administration of the chemotherapy to the MRE analysis and other factors. With that said, it is contemplated that MRE imaging may commence in less than four hours or up to several days following the administration of chemotherapy. In fact, it is contemplated that MRE imaging may be performed contemporaneously with or during chemotherapy administration. That is, chemotherapy may be administered to the patient while in the MR scanner and the present invention used to monitor the response of the patient to the chemotherapy in real time. By enabling the subject and the associated tumor to be imaged substantially immediately following or contemporaneously with chemotherapy, instead of waiting weeks, beyond the numerous advantages described above and hereafter, the present invention allows direct assessment, through imaging, of tissue/tumor stiffness and any increases thereof prior to large-scale cellular death (i.e. apoptosis) caused by chemotherapy. That is, the present invention, unlike traditional methods, can be performed very early when compared to prior-art methods to assess tissue/tumor stiffness even before cellular death affects stiffness.

Increased resolution can be obtained by using higher frequency shear waves in combination with small imaging fields of view. In addition, parallel imaging techniques which are often employed to increase acquisition speed can instead be applied to increase the spatial resolution of the MRE data set. For example, the present invention can utilize a powerful, high-frequency driver system to emit adequate high-frequency shear waves directed toward a small tumor and a high-frequency MRE SE or EPI, or other, pulse sequence designed to provide sufficient phase-signal-to-noise ratio to image high-frequency shear waves in the tumor. These two components in addition to mathematical inversion algorithms designed to spatially resolve shear modulus estimates are optimized for calculating the shear modulus of tumors whose dimensions are commonly less than, for example, 5 cm in length.

To further demonstrate the clinical viability of the present invention, DoHH2 tumor cells were injected (1×10$^7$ cells in 150μ) subcutaneously into the flank of genetically modified mice to induce tumor growth (DoHH2 is an EBV-negative, CD20 positive, human B-cell non-Hodgkin's lymphoma cell line that carries the t(14;18)(q32;q21) and was isolated from a patient with a transformed lymphoma). The tumor cells were maintained in RPMI 1640 medium supplemented with 10% heat-inactivated FCS (Sigma Chemical Co.), 50 U/ml penicillin G, 50 μg/ml gentamicin and 100 μg/ml streptomycin (all from Ufe Technologies, Grand Island, N.Y., USA) with the addition of 10 mM HEPES, 4.5 g/l glucose and 1 mM sodium pyruvate. A total of 11 Male CB17/SCID mice (Harlan Sprague Dawley, Indianapolis, Ind., USA), 6-8 weeks old, maintained in a pathogen-free environment were used for the study. Each time, 1-2 mice were picked up and administrated a chemotherapy drug and saline randomly. In total, (a) 6 tumors/mice were in the untreated control group (injected with phosphate buffered saline): (b) and 5 tumors/mice were in the chemo group (intraperitoneally injected with 4 mg of 160 mg/kg cyclophosphamide). Four hours later, the mice were killed with $CO_2$; the tumors were excised from the mice and IMRE data were obtained immediately.

Figure 5:
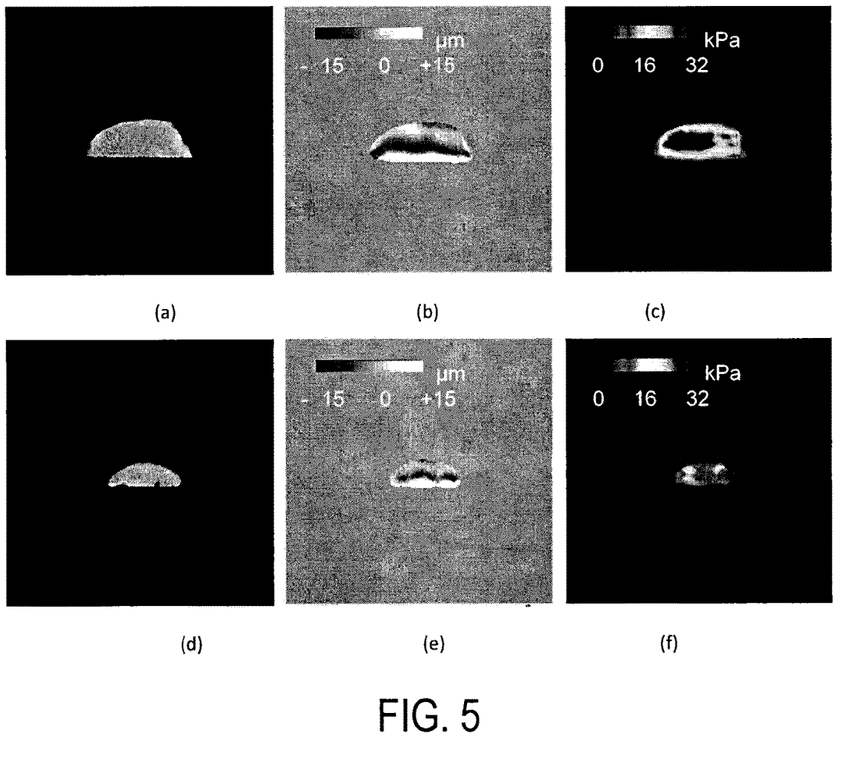
FIG. 5 is a series of images of tumors acquired in accordance with the present invention, where

FIG. 5 shows two typical examples of the MRE results. The top row (a-c) shows results of a tumor from a mouse treated with the chemotherapy drug and the lower row (d-f) shows results of a tumor treated with saline. Specifically, FIGS. 5a and 5d show $T_1$ weighted images of the tumors. FIGS. 5b and 5e show shear wave images of the tumors. Finally, FIGS. 5c and 5f show elastograms of the tumors. As can be seen in FIG. 5c, the tumor has, as reflected in the change in stiffness illustrated, responded to the receipt of the dose of chemotherapy. As can be seen in FIG. 5f, the tumor has, as reflected in the lack of change in stiffness illustrated, not responded to the dose of saline. Accordingly, the elastograms provide an indication and reporting of the effectiveness of the chemotherapy provided to the tumor, for example, by way of a color coding applied across the elastogram.

Table 1 shows the tumor stiffness values between the tumor groups treated with the chemotherapy drug and saline.

TABLE 1

| Group | Number | Mean (kPa) | Std. Error | −95% (kPa) | +95% (kPa) |
|---|---|---|---|---|---|
| Chemo | 5 | 21.82 | 2.85 | 13.92 | 29.72 |
| Control | 6 | 15.44 | 3.74 | 11.51 | 19.36 |

Figure 6:
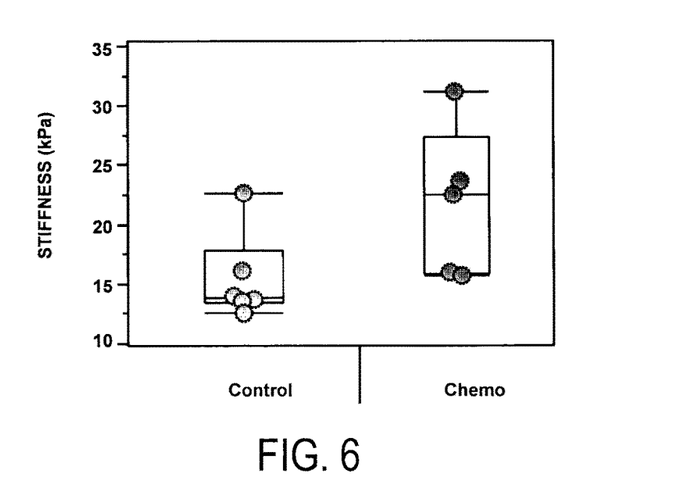
FIG. 6 is a graph of stiffness of both the control and chemotherapy groups illustrating that there is a statistically significant change in the tumor stiffness measured by MRE between the saline group and the chemotherapy group.

FIG. 6 shows the result of the one-sided T-test between the two groups whose p value was a statistically significant 0.034. The results showed that there was a significant change in the tumor stiffness measured by MRE between the mice administered with saline and with a chemotherapeutic agent. From these results, it is shown that the technique of monitoring the chemotherapy efficacy by measuring the tumor stiffness through MRE is readily clinically feasible.

To provide additional demonstrative data regarding the clinical viability of the present invention, 20 tumors were grown in genetically modified mice (6-8 weeks) using a subcutaneous injection of DoHH2 cells. The mice were divided into two groups, the first considered the "control" (N=7) and the second the chemotherapy or "chemo" (N=8) group. Five mice failed to grow tumors and were excluded from the study. Following an initial scan to determine baseline stiffness, the control group received an injection of normal saline while the chemo group received 4 mg of cyclophosphamide (160 mg/kg). MRE was performed on each mouse using an experimental setup specifically designed to accommodate the mouse and providing the mouse with the requisite anesthesia, via a constant flow of isofluorane during the image acquisition. MRE was performed at different time points (baseline to 4 days post-injection). The experimental setup included a high-frequency electromechanical driver that was developed to produce localized vibrations in the tumor within the mouse at a frequency of 800 Hz. All experiments were performed on a 3.0 T whole-body MRI scanner using a specialized 6-cm diameter transmit-receive RF coil and an EPI based MRE sequence. The MRE imaging parameters included FOV=5 cm; TR/TE=1100/99 msec; motion encoding gradient (MEG) frequency=800 Hz; MEG direction=SI, AP, RL; motion encoding sensitivity=3.98 μm/(π radians); BW=83.0 kHz. Volumetric measurements were obtained using both a caliper and measurements from a $T_2$-weighted image data set in order to quantify treatment response. Elastograms (stiffness maps) were calculated using a Multiple Model Direct Inversion (MMDI) algorithm with a directional filter (Butterworth bandpass filter with cutoff frequencies 2-128 waves/FOV).

Figure 7:
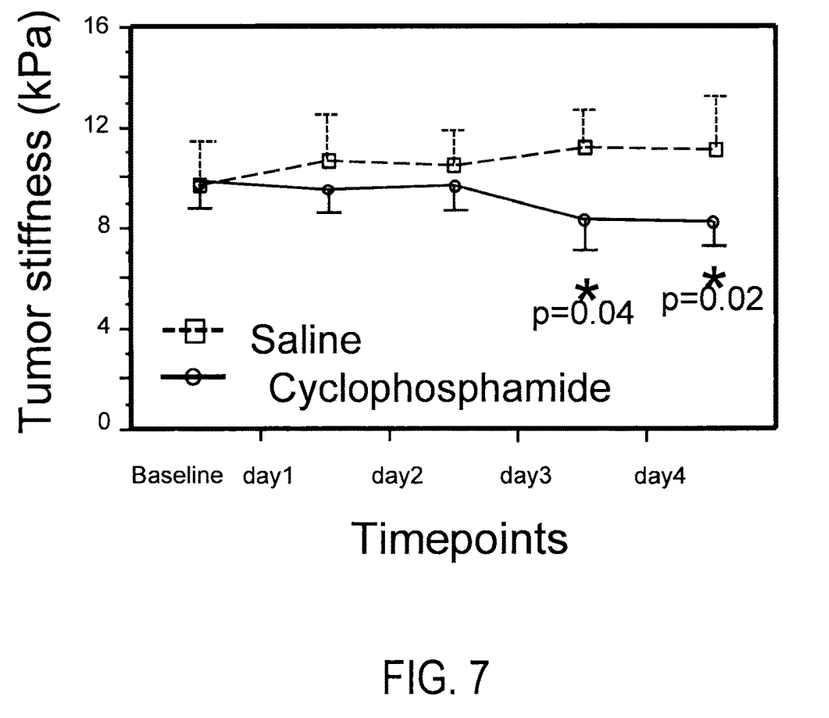
FIG. 7 is a graph showing a change in tumor stiffness measured in vivo after administration of chemotherapy (circle) and saline (square).

A representative sample of the reconstructed elastogram at baseline and day 4 for both a saline and a chemotherapy treated mouse tumor showed that, for the saline treated mice (N=7), the average shear stiffness from baseline to day 4 increased by 1.429 kPa (9.7029±1.12 kPa to 11.132±0.94). Alternatively, in the chemo mice (N=8) shear stiffness decreased on average by 1.649 kPa (9.885±1.74 kPa to 8.237±1.93 kPa). It is important to appreciate that the large standard deviation of the shear stiffness estimates is due mainly to inhomogeneities within the tumors as opposed to the MRE inversion method. A multiple comparison Tukey HSD test was performed and the results are shown in FIG. 7. In the chemo group, there was a significant change in stiffness from baseline at day 3 (p=0.04) and day 4 (p=0.02). No significant change in stiffness was observed in mouse tumors following administration of saline. Similarly, no statistically significant change in volume was observed in either the control or chemo group; however, the tumors in the control group tended to become larger (p=0.53) and tumors in the chemo group remained the same or decreased slightly (p=0.59). As addressed above, previous ex vivo mouse tumor studies suggested that stiffness increased in the chemo group 4 hours after drug administration. No changes in stiffness were observed in vivo at time points before three days after injection.

The present invention provide has been shown to provide a system and method for detecting a change in tumor stiffness in vivo within 3-4 days of drug administration and even earlier. Changes in tumor stiffness may be an early predictive biomarker for the effectiveness of a chemotherapy treatment, which may improve the individualized response-adaptive chemotherapy to reduce both short and long term side effects.

The present invention has been described in terms of one or more preferred embodiments, and it should be appreciated that many equivalents, alternatives, variations, and modifications, aside from those expressly stated, are possible and within the scope of the invention.

We claim:

1. A method for assessing an effectiveness of chemotherapy on a tumor within a subject following the administration of the chemotherapy to the subject, the method comprising the steps of:
   (a) arranging the subject within a magnetic resonance imaging (MRI) system;
   (b) coupling to the subject a magnetic resonance elastography (MRE) driver;
   (c) controlling the MRE driver and the MRI system using a pulse sequence to acquire raw MRE data from the tumor;
   (d) inverting the raw MRE data to produce an elastogram of the tumor;
   (e) selecting a region of interest in the elastogram;
   (f) quantifying a change in shear stiffness within at least a portion of the region of interest relative to a predetermined baseline shear stiffness;
   (g) indicating a response of the tumor to the chemotherapy using the change in shear stiffness determined in step (f);
   wherein step f) is timed relative to administration of the chemotherapy; and
   wherein step f) is performed at a time interval less than 4 hours following administration of the chemotherapy to the subject.

2. The method of claim 1 wherein step (g) includes indicating, in a color code, a response of the tumor to the chemotherapy as correlated to the change in shear stiffness within the at least a portion of the region of interest.

3. The method of claim 1 wherein step (f) includes determining mean shear stiffness.

4. The method of claim 3 wherein measuring the mean shear stiffness is measured for each slice acquired using the MM system and reporting a shear stiffness value of subportions of the at least a portion of the region of interest.

5. The method of claim 1 wherein step (c) includes using a high-frequency pulse sequence.

6. The method of claim 5 wherein the high-frequency pulse sequence includes a motion-encoding gradient (MEG) waveform having a frequency of approximately 800 Hz.

7. The method of claim 5 wherein the high-frequency pulse sequence includes a motion-encoding gradient (MEG) waveform having a frequency of approximately a kilohertz.

8. The method of claim 1 wherein step (f) includes determining a shear modulus of at least a portion of the tumor.

9. The method of claim 1 wherein step (g) includes determining a relative shear stiffness of at least a portion of the tumor to be increased.

* * * * *

UNITED STATES PATENT AND TRADEMARK OFFICE
CERTIFICATE OF CORRECTION

| | | |
|---|---|---|
| PATENT NO. | : 9,750,426 B2 | Page 1 of 1 |
| APPLICATION NO. | : 13/301300 | |
| DATED | : September 5, 2017 | |
| INVENTOR(S) | : McGee et al. | |

It is certified that error appears in the above-identified patent and that said Letters Patent is hereby corrected as shown below:

In the Specification

Column 7, Line 67, "viva" should be --vivo--.

Column 9, Line 25, "IMRE" should be --MRE--.

Column 10, Line 17, "TRITE" should be --TR/TE--.

In the Claims

Column 12, Claim 4, Line 9, "MM" should be --MRI--.

Signed and Sealed this
Seventh Day of November, 2017

Joseph Matal
*Performing the Functions and Duties of the*
*Under Secretary of Commerce for Intellectual Property and*
*Director of the United States Patent and Trademark Office*